(12) United States Patent
Li et al.

(10) Patent No.: US 11,124,816 B2
(45) Date of Patent: Sep. 21, 2021

(54) METHOD FOR IMPROVING THE TRANSPARENCY OF STARCH LIQUEFACTION

(71) Applicant: Jiangnan University, Wuxi (CN)

(72) Inventors: Zhaofeng Li, Wuxi (CN); Zhengbiao Gu, Wuxi (CN); Zhe Wang, Wuxi (CN); Caiming Li, Wuxi (CN); Sijia Xu, Wuxi (CN); Li Cheng, Wuxi (CN); Yan Hong, Wuxi (CN)

(73) Assignee: Jiangnan University, Wuxi (CN)

( * ) Notice: Subject to any disclaimer, the term of this patent is extended or adjusted under 35 U.S.C. 154(b) by 105 days.

(21) Appl. No.: 16/527,596

(22) Filed: Jul. 31, 2019

(65) Prior Publication Data

US 2019/0352686 A1 Nov. 21, 2019

Related U.S. Application Data

(63) Continuation of application No. PCT/CN2018/089938, filed on Jun. 5, 2018.

(30) Foreign Application Priority Data

Mar. 16, 2018 (CN) .......................... 201810219838.8

(51) Int. Cl.
*C12P 19/18* (2006.01)
*C12P 19/14* (2006.01)

(52) U.S. Cl.
CPC ............... *C12P 19/18* (2013.01); *C12P 19/14* (2013.01); *C12Y 204/01018* (2013.01)

(58) Field of Classification Search
CPC ..................................................... C12P 19/04
See application file for complete search history.

(56) References Cited

FOREIGN PATENT DOCUMENTS

| CN | 101631474 A | 1/2010 |
|---|---|---|
| CN | 106190998 A | 12/2016 |
| CN | 106367457 A | 2/2017 |
| CN | 107345234 A | 11/2017 |

OTHER PUBLICATIONS

Shinohara et al. Appl Microbiol Biotechnol, 2001, 57:653-659.*

* cited by examiner

*Primary Examiner* — Bin Shen
(74) *Attorney, Agent, or Firm* — IPro, PLLC

(57) ABSTRACT

The present disclosure disclosed is method for improving the transparency of starch liquefaction, and belongs to the field of biologically modified starch. The method changes the molecular structure of the starch liquefaction product by adding a 1,4-α-glucan branching enzyme from *Rhodothermus obamensis*, so the molecular structure has a smaller branched chain and a higher branching degree, thereby achieving the purpose of improving transparency and stability. The method comprises the steps of dissolving a starch liquefaction product in water according to a certain concentration to prepare an aqueous solution of the starch liquefaction product, and adding a 1,4-α-glucan branching enzyme to react at a certain temperature for a period of time, so as to improve the transparency of the starch liquefaction product during storage. The method provides a new idea for improving the stability of starch liquefaction products, and has great potential and application prospects.

10 Claims, 7 Drawing Sheets

Specification includes a Sequence Listing.

METHOD FOR IMPROVING THE TRANSPARENCY OF STARCH LIQUEFACTION

CROSS REFERENCE TO RELATED APPLICATIONS

This application claims priority to International Patent Application Number PCT/CN2018/089938 filed on Jun. 5, 2018, which claims priority to Chinese Patent Application CN 201810219838.8 filed on Mar. 16, 2018, the entirety of the contents of both of which are incorporated herein by reference.

INCORPORATION OF SEQUENCE LISTING

This application contains a sequence listing submitted in Computer Readable Form (CRF). The sequence listing contains one file called "seq.txt" which is 6 kilobytes in size and which was created on Jun. 22, 2021.

TECHNICAL FIELD

The disclosure herein relates to the field of biologically modified starch, relating to method for improving the transparency of starch liquefaction.

BACKGROUND

Starch liquefaction is catalytic hydrolysis of gelatinized starch into smaller dextrin, oligosaccharides, monosaccharide molecules, etc. by using medium or high temperature resistant α-amylase. In the hydrolysis process of the above starch, the content of reducing end continuously increases, and a DE value (dextrose equivalent) can be used to indicate the degree of hydrolysis of the starch. A starch liquefaction product has a DE value greater than or equal to 2, and a liquefied product having the DE value of 20 or less is generally referred to as maltodextrin. Compared with starch, the starch liquefaction product has higher solubility and stronger thickening effect and filling effect, which can be used as a substitute for fat or an embedding carrier for volatile substances, and has a different application range from the starch.

According to the degree of liquefaction of starch, starch liquefaction products with different DE values can be obtained. When the DE value is 4-7, the starch liquefaction product has the characteristics of soft taste, low sweetness, low hygroscopicity, etc., can be used as a thickener, a stabilizer, a filler, a carrier, etc. in food, is easily absorbed by the human body, and is suitable to serve as a basic raw material of food for patients and infants. When the DE value is 9-12, the starch liquefaction product is not easily damp and difficult to brown, and can be used in food to improve the touch of the food and produce high viscosity. When the DE value is 15-17, the starch liquefaction product has strong fluidity, good solubility and suitable viscosity, and can be applied to candy, beverage, instant food and canned food to improve solubility, reduce sweetness, improve product flavor and improve product quality. However, because macromolecular substances with low branching degree in the starch liquefaction product will be re-associated, the starch liquefaction will gradually become turbid during storage, resulting in retrogradation, which causes reduced transparency and stability of the starch liquefaction product, and further affects the appearance, taste, color and the like of the product using the starch liquefaction product. This instability of the starch liquefaction product during storage limits its application.

The 1,4-α-glucan branching enzyme (GBE; EC 2.4.1.18) is a kind of glycosyltransferase, and is an important enzyme in the field of bio-enzymatic modification of starch. It catalyzes cleavage of an α-1,4-glycosidic bond in linear or branched chain molecules of starch, resulting in short chains with non-reducing ends. The short chain cut under the action of transglycosylation acts on a receptor chain in the form of an α-1,6-glycosidic bond, thereby forming a new α-1,6-linked branch point on the original main chain.

SUMMARY

The present disclosure provides method for improving the transparency of starch liquefaction, comprising: carrying out treatment on a starch liquefaction product having the DE value of 20 or less by using 1,4-α-glucan branching enzyme, wherein the starch liquefaction product refers to a mixture of short-chain small molecule dextrin (the carbon chain length of short-chain small molecule dextrin is 1-35; the higher the DE value, correspondingly, the shorter the carbon chain length), oligosaccharides and monosaccharide molecules obtained by hydrolyzing a long carbon chain of starch with an amylolytic enzyme such as a medium temperature or high temperature resistant α-amylase; and the 1,4-α-glucan branching enzyme is derived from *Rhodothermus obamensis*. In fact, the method provided by the present disclosure is also capable of improving the transparency of starch liquefaction product having a DE value greater than 20, except that the transparency of starch liquefaction product having a DE value greater than 20 is already relatively high and generally does not require further improvement.

In one embodiment of the present disclosure, the sequence of the gene encoding the 1,4-α-glucan branching enzyme is as shown in GenBank: AB060080.1 (SEQ ID NO:1).

In one embodiment of the present disclosure, the method specifically comprises: the starch liquefaction product is dissolved in water according to a certain concentration for preparing an aqueous solution of the starch liquefaction product, the 1,4-α-glucan branching enzyme is added for reacting at a certain temperature for a period of time, and enzyme deactivation is carried out by boiling. The aqueous solution of the starch liquefaction product has the concentration of 1-40% (w/v, weight of starch liquefaction product in gram/100 mL of water). The pH of the aqueous solution of the starch liquefaction product is 5.5-7.5. The reaction temperature is 50-70° C., and the reaction time is 4-24 h.

In one embodiment of the present disclosure, the DE value of the starch liquefaction product is 20 or less.

In one embodiment of the present disclosure, the starch is ordinary corn starch, potato starch, tapioca starch, sweet potato starch, rice starch or wheat starch.

In one embodiment of the present disclosure, the 1,4-α-glucan branching enzyme is added in the amount of 30-500 U/g of starch liquefaction product on a dry basis.

In one embodiment of the present disclosure, the starch liquefaction product having the DE value of 4 is dissolved in water to prepare a 5% (w/v, g/100 mL) aqueous solution of the starch liquefaction product, the pH is adjusted to 6.5, the 1,4-α-glucan branching enzyme is added in the amount of 30 U/g on a dry basis, treatment is carried out at 60° C. for 8 h, and enzyme deactivation is carried out by boiling.

In one embodiment of the present disclosure, the starch liquefaction product having the DE value of 7 is dissolved in water to prepare a 5% (w/v, g/100 mL) aqueous solution of the starch liquefaction product, the pH is adjusted to 7.5, the 1,4-α-glucan branching enzyme is added in the amount of 100 U/g on a dry basis, treatment is carried out at 50° C. for 12 h, and enzyme deactivation is carried out by boiling.

In one embodiment of the present disclosure, the starch liquefaction product having the DE value of 11 is dissolved in water to prepare a 20% (w/v, g/100 mL) aqueous solution of the starch liquefaction product, the pH is adjusted to 7.0, the 1,4-α-glucan branching enzyme is added in the amount of 200 U/g on a dry basis, treatment is carried out at 55° C. for 24 h, and enzyme deactivation is carried out by boiling.

In one embodiment of the present disclosure, the starch liquefaction product having the DE value of 15 is dissolved in water to prepare a 35% (w/v, g/100 mL) aqueous solution of the starch liquefaction product, the pH is adjusted to 7.0, the 1,4-α-glucan branching enzyme is added in the amount of 500 U/g on a dry basis, treatment is carried out at 65° C. for 24 h, and enzyme deactivation is carried out by boiling.

The macromolecular substances with low branching degree in the starch liquefaction product having a low DE value are easily re-associated, resulting in retrogradation, which causes the transparency and stability of the starch liquefaction product get worse during storage, and further adversely affects the appearance, taste, color and the like of the product using the starch liquefaction product. The method adopts the 1,4-α-glucan branching enzyme to treat the starch liquefaction product having the DE value of 20 or less, to hydrolyze an α-1,4-glycosidic bond to form an α-1,6-glycosidic bond, and transform a slender starch molecular structure into a chunky molecular structure to form a tighter branch structure. After the starch liquefaction product is modified by the 1,4-α-glucan branching enzyme, the transparency is improved during storage, especially during continuous storage at 4° C. After storage is performed for 30 days at 4° C., the transparency can still reach 99.0% or more.

The 1,4-α-glucan branching enzyme from *Rhodothermus obamensis* has a significantly better effect on improving the transparency of the starch liquefaction product than the 1,4-α-glucan branching enzymes from *Geobacillus thermoglucosidans* and rice.

Gelatinization of starch refers to the process in which starch granules absorb water, dissolve and swell and cleave at a high temperature to form a homogeneous paste-like solution, in which only a very slight hydrolysis reaction occurs. If a starch gelatinization product is treated with a 1,4-α-glucan branching enzyme, only the transient transparency of the gelatinization product can be improved, and the transparency of the starch gelatinization product in a continuous storage process cannot be improved.

DETAILED DESCRIPTION

Figure 1:
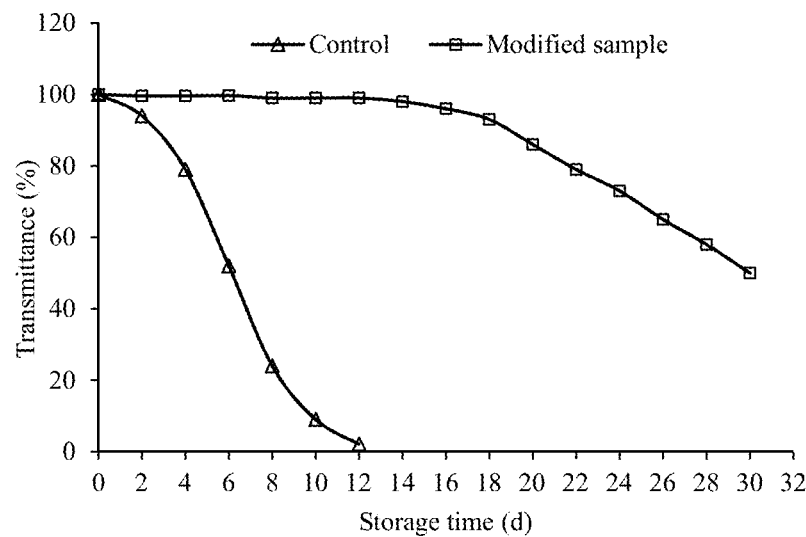
FIG. 1 is a graph showing the effect of modification for 4 h of the 1,4-α-glucan branching enzyme from *Rhodothermus obamensis* on the transparency of a 5% (w/v) starch liquefaction product having the DE value of 4, with water transparency as 100%.

Transparency is represented by transmittance measured at 620 nm by using a spectrophotometer. The spectrophotometer is capable of exhibiting the transmittance of a measured sample with respect to water having a transmittance of 100%.

EXAMPLE 1

The production and the preparation of the 1,4-α-glucan branching enzyme from *Rhodothermus obamensis* comprise the following three steps:

(1) Seed culture: according to an inoculum size of 0.2% (v/v), 100 μL of a glycerol strain *Escherichia coli*/pET-20b (+)/gbe (*Escherichia coli* containing a vector pET-20b(+)/gbe carrying a gene encoding a 1,4-α-glucan branching enzyme from *Rhodothermus obamensis*) preserved at −80° C. is inoculated in a 250 mL Erlenmeyer flask containing 50 mL of LB medium (containing 5 g/L yeast extract, 10 g/L tryptone and 10 g/L NaCl, and pH of 7.0), and cultured for 8-10 h (at 200 r/min) on a 37° C. shaker. Before inoculation, ampicillin with the final concentration of 100 μg/mL is added to the LB medium.

(2) Fermentation culture: the activated seed solution is transferred into a 250 mL Erlenmeyer flask containing 50 mL of TB medium (containing 24 g/L yeast extract, 12 g/L tryptone, 5 g/L glycerol, 17 mM $KH_2PO_4$ and 72 mM $K_2HPO_4$, and pH of 7.0) according to an inoculum size of 2% (v/v), and cultured on a 37° C. shaker at 200 r/min. When the thalli are cultured until the $OD_{600}$ is 0.5-0.6, IPTG with the final concentration of 0.05 mM is added, and the culture is continued for 48 h. Before inoculation, ampicillin with the final concentration of 100 μg/mL is added to the TB medium. After fermentation, the fermentation medium is centrifuged at 4° C., 10,000×g for 15 min, and the supernatant is collected to obtain a crude enzyme solution.

(3) Purification: the obtained crude enzyme solution is purified by nickel column one-step affinity chromatography to obtain a pure enzyme solution of the 1,4-α-glucan branching enzyme from *Rhodothermus obamensis* with a specific activity of 6,650.7 U/mg.

EXAMPLE 2

The production and the preparation of the 1,4-α-glucan branching enzyme from *Geobacillus thermoglucosidans* comprise the following three steps:

(1) Seed culture: according to an inoculum size of 0.2% (v/v), 100 μL of a glycerol strain *Escherichia coli*/pET-20b (+)/gbe (*Escherichia coli* containing an expression vector pET-20b(+)/gbe carrying a gene encoding a 1,4-α-glucan branching enzyme from *Geobacillus thermoglucosidans*) preserved at −80° C. is inoculated in a 250 mL Erlenmeyer flask containing 50 mL of LB medium (containing 5 g/L yeast extract, 10 g/L tryptone and 10 g/L NaCl, pH of 7.0), and cultured for 8-10 h (at 200 r/min) on a 37° C. shaker. Before inoculation, ampicillin with the final concentration of 100 μg/mL is added to the LB medium.

(2) Fermentation culture: the activated seed solution is transferred into a 250 mL Erlenmeyer flask containing 50 mL of TB medium (containing 24 g/L yeast extract, 12 g/L tryptone, 5 g/L glycerol, 17 mM $KH_2PO_4$ and 72 mM of $K_2HPO_4$, and pH of 7.0) according to an inoculum size of 2% (v/v), and oscillated and cultured on a 30° C. shaker at 200 r/min for 48 h. Before inoculation, ampicillin with the final concentration of 100 μg/mL is added to the TB medium. After fermentation, the fermentation medium is centrifuged at 4° C., 10,000×g for 15 min, and the supernatant is collected to obtain a crude enzyme solution.

(3) Purification: the obtained crude enzyme solution is purified by nickel column one-step affinity chromatography to obtain a pure enzyme solution of the 1,4-α-glucan branching enzyme from *Geobacillus thermoglucosidans* with a specific activity of 2,005.1 U/mg.

EXAMPLE 3

The starch liquefaction product having the DE value of 4 is dissolved in water to prepare a 5% (w/v) aqueous solution of the starch liquefaction product, the pH is adjusted to 6.5, the 1,4-α-glucan branching enzyme from *Rhodothermus obamensis* is added in the amount of 30 U/g on a dry basis, treatment is carried out at 60° C. for 4 h, and enzyme deactivation is carried out by boiling. The obtained product is stored in the environment of 4° C., and is measured for transparency at intervals. The results of transparency measurement are shown in FIG. 1, and the control represents an unmodified starch liquefaction product with the same concentration.

The results in FIG. 1 show that the transparency of the starch liquefaction product modified by the 1,4-α-glucan branching enzyme for 4 h and stored at 4° C. for 30 d is always 50% or more, and the transparency can reach 50.0% after the product is stored for 30 d. The unmodified starch liquefaction product is completely turbid after stored at 4° C. for 12 d.

EXAMPLE 4

The starch liquefaction product having the DE value of 4 is dissolved in water to prepare a 5% (w/v) aqueous solution of the starch liquefaction product, the pH is adjusted to 6.5, the 1,4-α-glucan branching enzyme from *Rhodothermus obamensis* is added in the amount of 30 U/g on a dry basis, treatment is carried out at 60° C. for 8 h, and enzyme deactivation is carried out by boiling. The obtained product is stored in the environment of 4° C., and is measured for transparency at intervals. The results of transparency measurement are shown in FIG. 2, and the control represents an unmodified starch liquefaction product with the same concentration.

Figure 2:
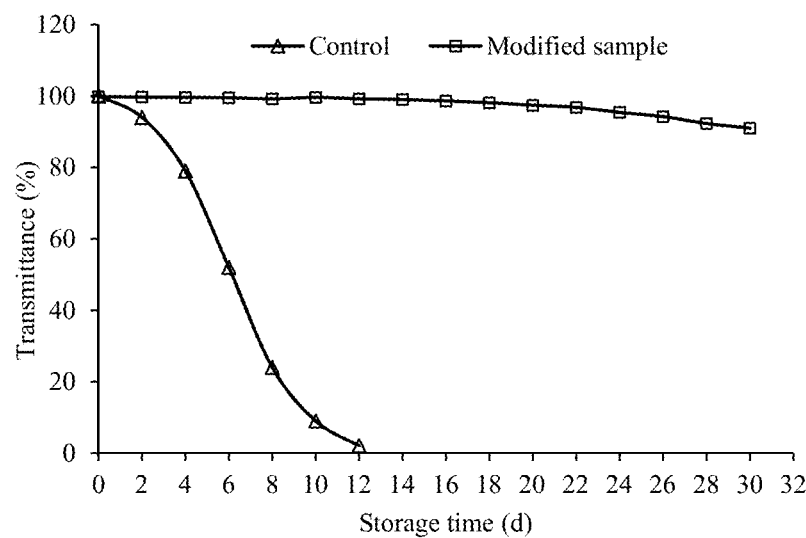
FIG. 2 is a graph showing the effect of modification for 8 h of the 1,4-α-glucan branching enzyme from *Rhodothermus obamensis* on the transparency of a 5% (w/v) starch liquefaction product having the DE value of 4, with water transparency as 100%.

The results in FIG. 2 show that the transparency of the starch liquefaction product modified by the 1,4-α-glucan branching enzyme for 8 h and stored at 4° C. for 30 d is always 90% or more, and the transparency can reach 91.0% after the product is stored at 4° C. for 30 d. The unmodified starch liquefaction product with the concentration of 5% (w/v) and the DE value of 4 is completely turbid after stored at 4° C. for 12 d.

EXAMPLE 5

The starch liquefaction product having the DE value of 7 is dissolved in water to prepare a 5% (w/v) aqueous solution of the starch liquefaction product, the pH is adjusted to 7.5, the 1,4-α-glucan branching enzyme from *Rhodothermus obamensis* is added in the amount of 100 U/g on a dry basis, treatment is carried out at 50° C. for 12 h, and enzyme deactivation is carried out by boiling. The obtained product is stored in the environment of 4° C., and is measured for transparency at intervals. The results of transparency measurement are shown in FIG. 3, and the control represents an unmodified starch liquefaction product with the same concentration.

Figure 3:
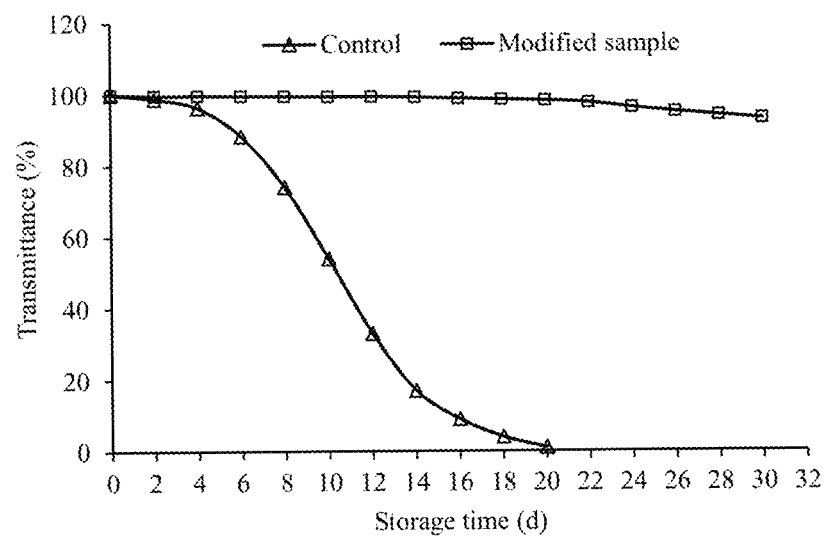
FIG. 3 is a graph showing the effect of the 1,4-α-glucan branching enzyme from *Rhodothermus obamensis* on the transparency of a 5% (w/v) starch liquefaction product having the DE value of 7, with water transparency as 100%.

The results in FIG. 3 show that the transparency of the starch liquefaction product modified by the 1,4-α-glucan branching enzyme for 12 h and stored at 4° C. for 30 d is always 90% or more, and the transparency can reach 93.2% after the product is stored at 4° C. for 30 d. The unmodified starch liquefaction product with the concentration of 5% (w/v) and the DE value of 7 is completely turbid after stored at 4° C. for 20 d.

EXAMPLE 6

The starch liquefaction product having the DE value of 7 is dissolved in water to prepare a 10% (w/v) aqueous solution of the starch liquefaction product, the pH is adjusted to 6.0, the 1,4-α-glucan branching enzyme from *Rhodothermus obamensis* is added in the amount of 200 U/g on a dry basis, treatment is carried out at 65° C. for 12 h, and enzyme deactivation is carried out by boiling. The obtained product is stored in the environment of 4° C., and is measured for transparency at intervals. The results of transparency measurement are shown in FIG. 4, and the control represents an unmodified starch liquefaction product with the same concentration.

Figure 4:
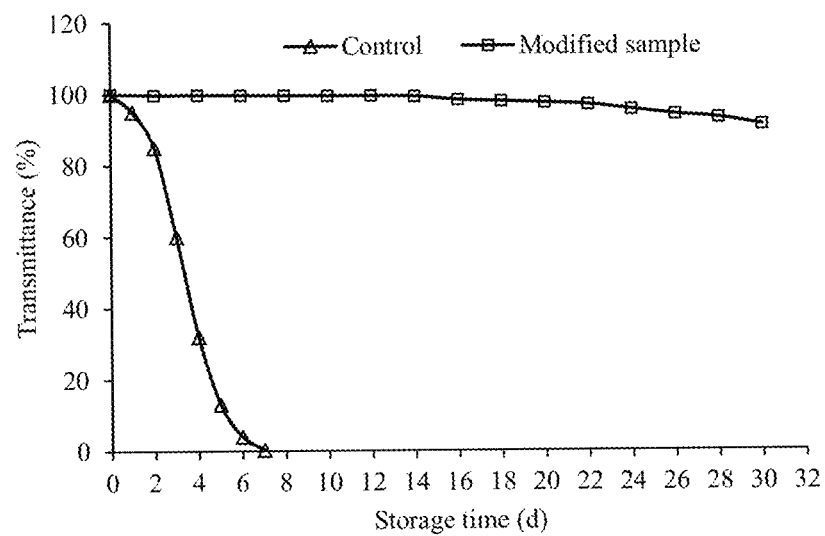
FIG. 4 is a graph showing the effect of the 1,4-α-glucan branching enzyme from *Rhodothermus obamensis* on the transparency of a 10% (w/v) starch liquefaction product having the DE value of 7, with water transparency as 100%.

The results in FIG. 4 show that the transparency of the starch liquefaction product modified by the 1,4-α-glucan branching enzyme for 12 h and stored at 4° C. for 30 d is always 90% or more, and the transparency can reach 90.8% after the product is stored at 4° C. for 30 d. The unmodified starch liquefaction product with the concentration of 10% (w/v) and the DE value of 7 is completely turbid after stored at 4° C. for 7 d.

EXAMPLE 7

The starch liquefaction product having the DE value of 11 is dissolved in water to prepare a 20% (w/v) aqueous solution of the starch liquefaction product, the pH is adjusted to 7.0, the 1,4-α-glucan branching enzyme from *Rhodothermus obamensis* is added in the amount of 200 U/g on a dry basis, treatment is carried out at 55° C. for 24 h, and enzyme deactivation is carried out by boiling. The obtained product is stored in the environment of 4° C., and is measured for transparency at intervals. The results of transparency measurement are shown in FIG. 5, and the control represents an unmodified starch liquefaction product with the same concentration.

Figure 5:
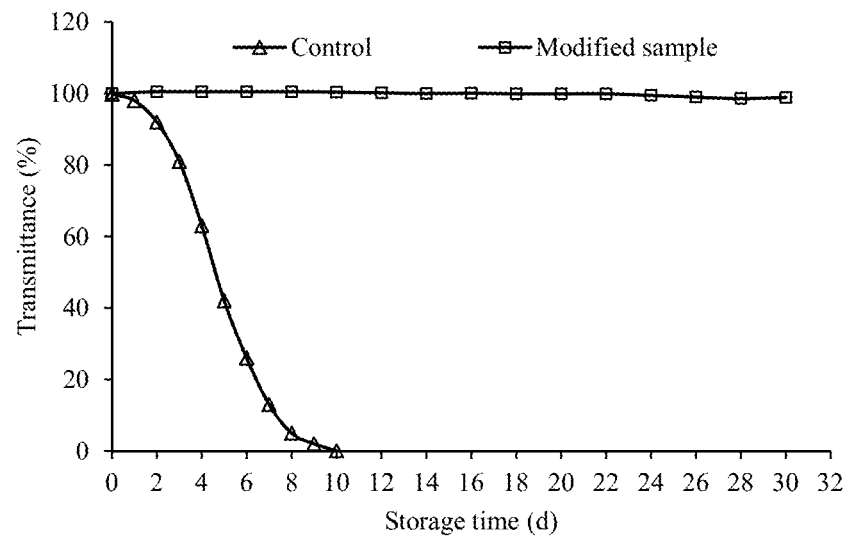
FIG. 5 is a graph showing the effect of the 1,4-α-glucan branching enzyme from *Rhodothermus obamensis* on the transparency of a 20% (w/v) starch liquefaction product having the DE value of 11, with water transparency as 100%.

The results in FIG. 5 show that the transparency of the starch liquefaction product modified by the 1,4-α-glucan branching enzyme and stored at 4° C. for 30 d is always about 100%, and the transparency can reach 99.1% after the product is stored at 4° C. for 30 d. The unmodified starch liquefaction product with the concentration of 20% (w/v) and the DE value of 11 is completely turbid after stored at 4° C. for 10 d.

EXAMPLE 8

The starch liquefaction product having the DE value of 11 is dissolved in water to prepare a 30% (w/v) aqueous solution of the starch liquefaction product, the pH is adjusted to 5.5, the 1,4-α-glucan branching enzyme from *Rhodothermus obamensis* is added in the amount of 300 U/g on a dry basis, treatment is carried out at 70° C. for 24 h, and enzyme deactivation is carried out by boiling. The obtained product is stored in the environment of 4° C., and is measured for transparency at intervals. The results of transparency measurement are shown in FIG. 6, and the control represents an unmodified starch liquefaction product with the same concentration.

Figure 6:
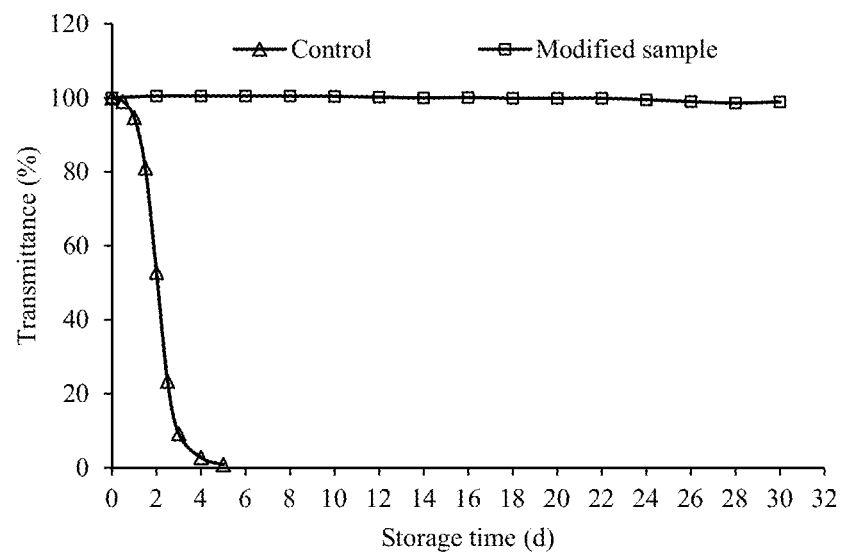
FIG. 6 is a graph showing the effect of the 1,4-α-glucan branching enzyme from *Rhodothermus obamensis* on the transparency of a 30% (w/v) starch liquefaction product having the DE value of 11, with water transparency as 100%.

The results in FIG. 6 show that the transparency of the starch liquefaction product modified by the 1,4-α-glucan branching enzyme and stored at 4° C. for 30 d is always about 100%, and the transparency can reach 99.0% after the product is stored at 4° C. for 30 d. The unmodified starch liquefaction product with the concentration of 30% (w/v) and the DE value of 11 is completely turbid after stored at 4° C. for 5 d.

EXAMPLE 9

The starch liquefaction product having the DE value of 15 is dissolved in water to prepare a 35% (w/v) aqueous solution of the starch liquefaction product, the pH is adjusted to 7.0, the 1,4-α-glucan branching enzyme from *Rhodothermus obamensis* is added in the amount of 500 U/g on a dry basis, treatment is carried out at 65° C. for 24 h, and enzyme deactivation is carried out by boiling. The obtained product is stored in the environment of 4° C., and is measured for transparency at intervals. The results of transparency measurement are shown in FIG. 7, and the control represents an unmodified starch liquefaction product with the same concentration.

Figure 7:
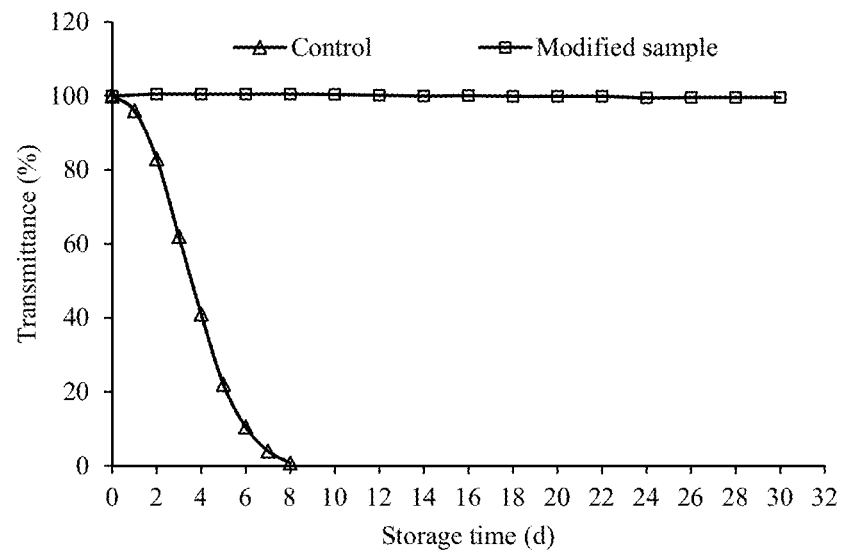
FIG. 7 is a graph showing the effect of the 1,4-α-glucan branching enzyme from *Rhodothermus obamensis* on the transparency of a 35% (w/v) starch liquefaction product having the DE value of 15, with water transparency as 100%.

The results in FIG. 7 show that the transparency of the starch liquefaction product modified by the 1,4-α-glucan branching enzyme and stored at 4° C. for 30 d is always about 100%, and the transparency can reach 99.3% after the product is stored at 4° C. for 30 d. The unmodified starch liquefaction product with the concentration of 35% (w/v) and the DE value of 15 is completely turbid after stored at 4° C. 8 d.

EXAMPLE 10

The starch liquefaction product having the DE value of 15 is dissolved in water to prepare a 40% (w/v) aqueous solution of the starch liquefaction product, the pH is adjusted to 7.0, the 1,4-α-glucan branching enzyme from *Rhodothermus obamensis* is added in the amount of 500 U/g on a dry basis, treatment is carried out at 65° C. for 24 h, and enzyme deactivation is carried out by boiling. The obtained product is stored in the environment of 4° C., and is measured for transparency at intervals. The results of transparency measurement are shown in FIG. 8, and the control represents an unmodified starch liquefaction product with the same concentration.

Figure 8:
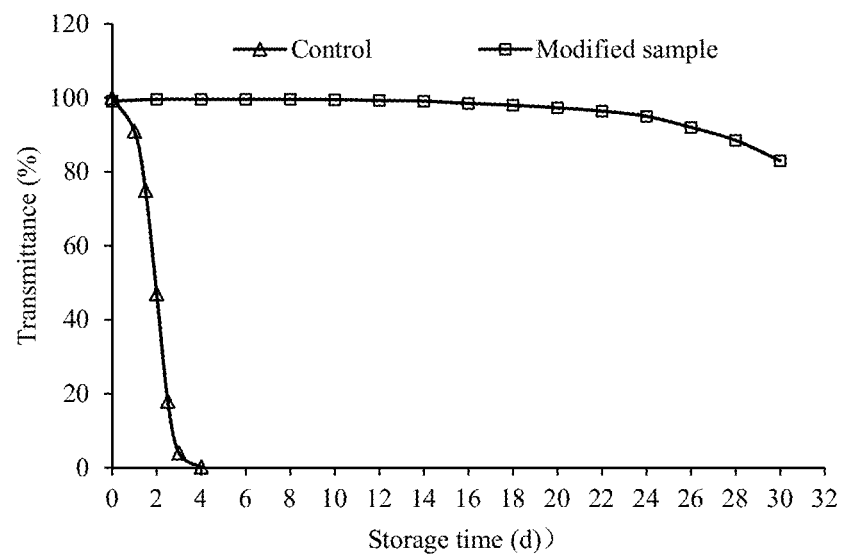
FIG. 8 is a graph showing the effect of the 1,4-α-glucan branching enzyme from *Rhodothermus obamensis* on the transparency of a 40% (w/v) starch liquefaction product having the DE value of 15, with water transparency as 100%.

The results in FIG. 8 show that the transparency of the starch liquefaction product modified by the 1,4-α-glucan branching enzyme and stored at 4° C. for 30 d is always 80% or more, and the transparency can reach 83.0% after the product is stored at 4° C. for 30 d. The unmodified starch liquefaction product with the concentration of 40% (w/v) and the DE value of 15 is completely turbid after stored at 4° C. for 4 d.

Comparing the results of the present example with the results of Example 9, it can be seen that when the concentration of the starch liquefaction product is 40%, the modification effect of the 1,4-α-glucan branching enzyme on the product is lowered, so the concentration of the starch liquefaction product shall be not higher than 35%.

COMPARATIVE EXAMPLE 1

The starch liquefaction product having the DE value of 4 is dissolved in water to prepare a 30% (w/v) aqueous solution of the starch liquefaction product, the pH is adjusted to 6.5, the 1,4-α-glucan branching enzyme from *Geobacillus thermoglucosidans* is added in the amount of 0.12 U/g on a dry basis, treatment is carried out at 45° C. for 4 h, and enzyme deactivation is carried out by boiling. The obtained product is stored in the environment of 4° C., and is measured for transparency at intervals. The results of transparency measurement are shown in FIG. 9, and the control represents an unmodified starch liquefaction product with the same concentration.

Figure 9:
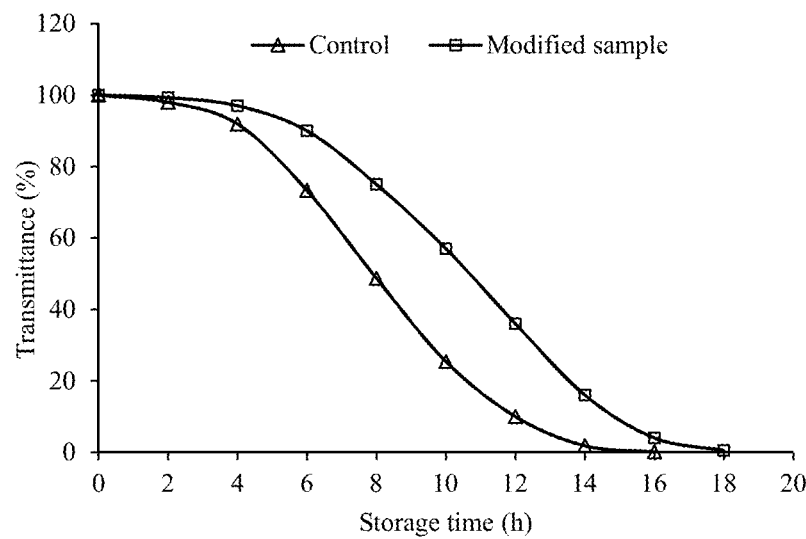
FIG. 9 is a graph showing the effect of the 1,4-α-glucan branching enzyme from *Geobacillus thermoglucosidans* on the transparency of a 30% (w/v) starch liquefaction product having the DE value of 4, with water transparency as 100%.

The results in FIG. 9 show that the 1,4-α-glucan branching enzyme from *Geobacillus thermoglucosidans* has a poor modification effect on the starch liquefaction product having the DE value of 4. The unmodified starch liquefaction product having the DE value of 4 is completely turbid after stored at 4° C. for 16 h, the completely turbid time of the modified starch liquefaction product is prolonged from 16 h to 18 h only, and the effect is poor.

COMPARATIVE EXAMPLE 2

The starch liquefaction product having the DE value of 7 is dissolved in water to prepare a 30% (w/v) aqueous solution of the starch liquefaction product, the pH is adjusted to 6.5, the 1,4-α-glucan branching enzyme from *Geobacillus thermoglucosidans* is added in the amount of 0.12 U/g on a dry basis, treatment is carried out at 45° C. for 4 h, and enzyme deactivation is carried out by boiling. The obtained product is stored in the environment of 4° C., and is measured for transparency at intervals. The results of transparency measurement are shown in FIG. 10, and the control represents an unmodified starch liquefaction product with the same concentration.

Figure 10:
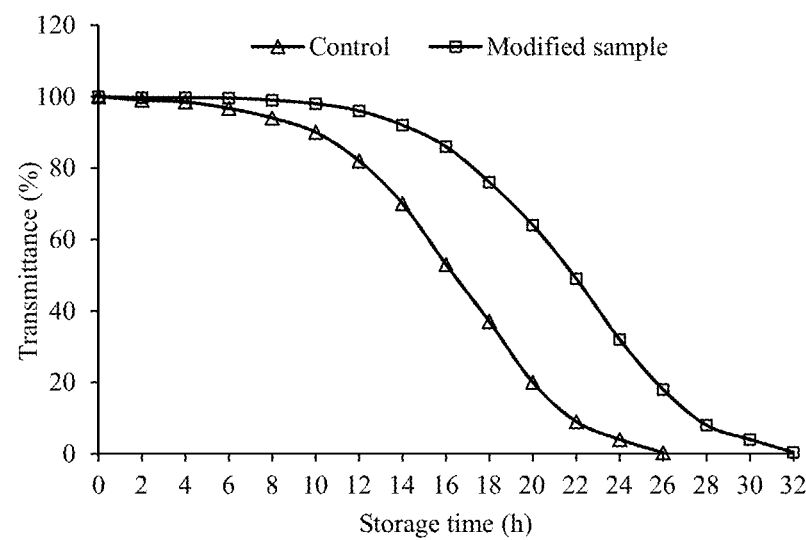
FIG. 10 is a graph showing the effect of the 1,4-α-glucan branching enzyme from *Geobacillus thermoglucosidans* on the transparency of a 30% (w/v) starch liquefaction product having the DE value of 7, with water transparency as 100%.

The results in FIG. 10 show that the 1,4-α-glucan branching enzyme from *Geobacillus thermoglucosidans* has a poor modification effect on the starch liquefaction product having the DE value of 7. The unmodified starch liquefaction product having the DE value of 7 is completely turbid after stored at 4° C. for 26 h, the completely turbid time of the modified starch liquefaction product is prolonged from 26 h to 32 h only, and the effect is poor.

COMPARATIVE EXAMPLE 3

The starch liquefaction product having the DE value of 11 is dissolved in water to prepare a 30% (w/v) aqueous solution of the starch liquefaction product, the pH is adjusted to 6.5, the 1,4-α-glucan branching enzyme from *Geobacillus thermoglucosidans* is added in the amount of 0.12 U/g on a dry basis, treatment is carried out at 45° C. for 4 h, and enzyme deactivation is carried out by boiling. The obtained product is stored in the environment of 4° C., and is measured for transparency at intervals. The results of transparency measurement are shown in FIG. 11, and the control represents an unmodified starch liquefaction product with the same concentration.

Figure 11:
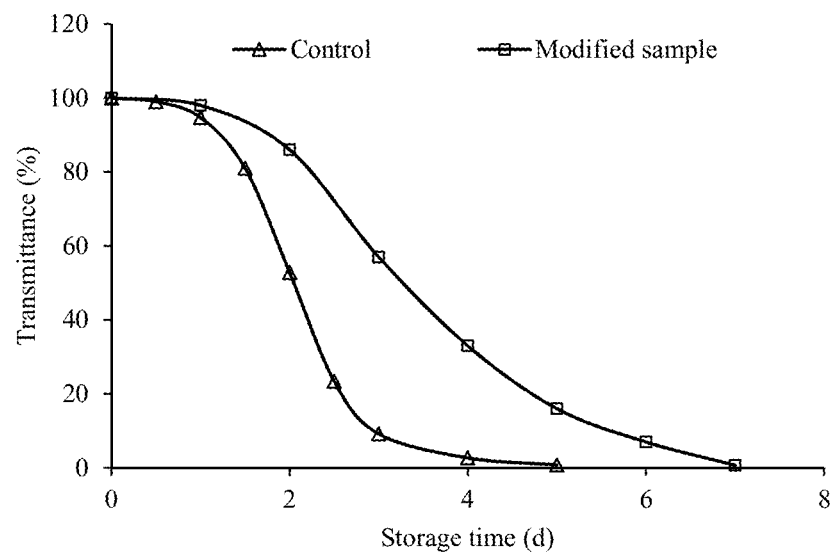
FIG. 11 is a graph showing the effect of the 1,4-α-glucan branching enzyme from *Geobacillus thermoglucosidans* on the transparency of a 30% (w/v) starch liquefaction product having the DE value of 11, with water transparency as 100%.

The results in FIG. 11 show that the 1,4-α-glucan branching enzyme from *Geobacillus thermoglucosidans* has a poor modification effect on the starch liquefaction product having the DE value of 11. The unmodified starch liquefaction product having the DE value of 11 is completely turbid after stored at 4° C. for 5 d, and the completely turbid time of the modified starch liquefaction product is prolonged from 5 d to 7 d only. While when the 1,4-α-glucan branching enzyme from *Rhodothermus obamensis* of the present disclosure is used for carrying out modification, the transparency of the modified starch liquefaction product can still reach 99.0% after the product is stored at 4° C. for 30 d.

COMPARATIVE EXAMPLE 4

Figure 12:
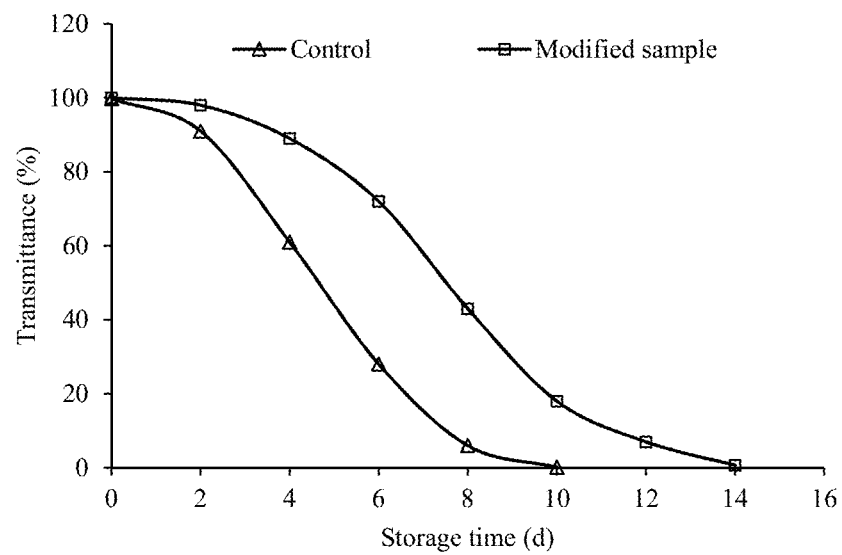
FIG. 12 is a graph showing the effect of the 1,4-α-glucan branching enzyme from *Geobacillus thermoglucosidans* on the transparency of a 30% (w/v) starch liquefaction product having the DE value of 15, with water transparency as 100%.

The starch liquefaction product having the DE value of 15 is dissolved in water to prepare a 30% (w/v) aqueous solution of the starch liquefaction product, the pH is adjusted to 6.5, the 1,4-α-glucan branching enzyme from *Geobacillus thermoglucosidans* is added in the amount of 0.12 U/g on a dry basis, treatment is carried out at 45° C. for 4 h, and enzyme deactivation is carried out by boiling. The obtained product is stored in the environment of 4° C., and is measured for transparency at intervals. The results of transparency measurement are shown in FIG. 12, and the control represents an unmodified starch liquefaction product with the same concentration.

The reaction results show that the 1,4-α-glucan branching enzyme from *Geobacillus thermoglucosidans* has a poor modification effect on the starch liquefaction product having the DE value of 15. The unmodified starch liquefaction product having the DE value of 15 is completely turbid after stored at 4° C. for 10 d, the completely turbid time of the modified starch liquefaction product is prolonged from 10 d to 14 d only, and the effect is poor.

COMPARATIVE EXAMPLE 5

The starch liquefaction product having the DE value of 7 is dissolved in water to prepare a 6% (w/v) aqueous solution of the starch liquefaction product, the pH is adjusted to 6.5, the 1,4-α-glucan branching enzyme from rice is added in the amount of 4 U/g on a dry basis, treatment is carried out at 45° C. for 3 h, and enzyme deactivation is carried out by boiling. The obtained product is stored in the environment of 4° C., and is measured for transparency at intervals. The results of transparency measurement are shown in FIG. 13, and the control represents an unmodified starch liquefaction product with the same concentration.

Figure 13:
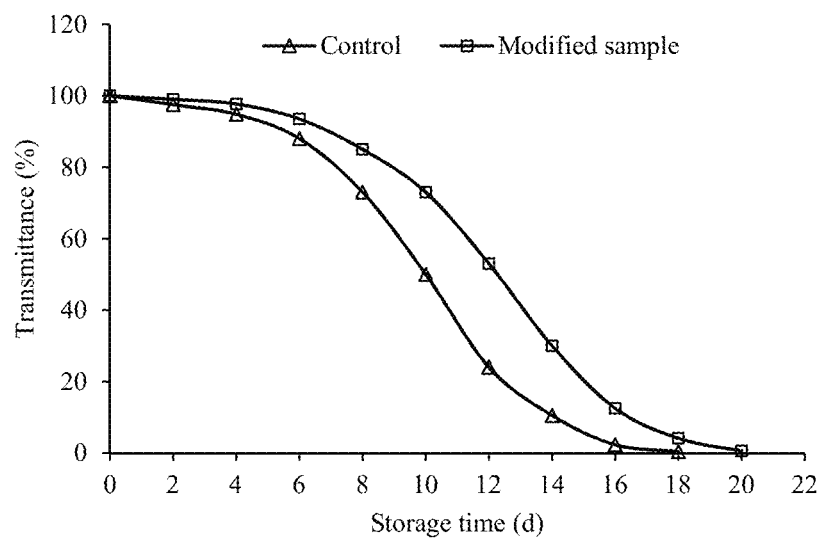
FIG. 13 is a graph showing the effect of the 1,4-α-glucan branching enzyme from rice on the transparency of a 6% (w/v) starch liquefaction product having the DE value of 7, with water transparency as 100%.

The results in FIG. 13 show that the 1,4-α-glucan branching enzyme from rice has a poor modification effect on the starch liquefaction product having the DE value of 7. The unmodified starch liquefaction product having the DE value of 7 is completely turbid after stored at 4° C. for 18 d, the completely turbid time of the modified starch liquefaction product is prolonged from 18 d to 20 d, and the effect is poor.

COMPARATIVE EXAMPLE 6

The starch liquefaction product having the DE value of 15 is dissolved in water to prepare a 6% (w/v) aqueous solution of the starch liquefaction product, the pH is adjusted to 7.5, the 1,4-α-glucan branching enzyme from rice is added in the amount of 6 U/g on a dry basis, treatment is carried out at 60° C. for 5 h, and enzyme deactivation is carried out by boiling. The obtained product is stored in the environment of 4° C., and is measured for transparency at intervals. The results of transparency measurement are shown in FIG. 14, and the control represents an unmodified starch liquefaction product with the same concentration.

Figure 14:
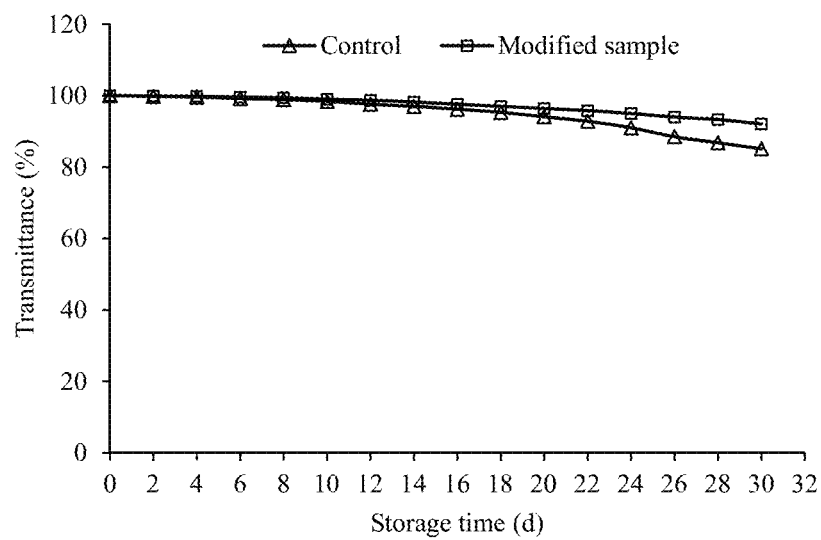
FIG. 14 is a graph showing the effect of the 1,4-α-glucan branching enzyme from rice on the transparency of a 6% (w/v) starch liquefaction product having the DE value of 15, with water transparency as 100%.

The results in FIG. 14 show that the 1,4-α-glucan branching enzyme from rice has a poor modification effect on the starch liquefaction product having the DE value of 15. The transparency of the unmodified starch liquefaction product having the DE value of 15 is 85.1% after the product is stored at 4° C. for 30 d, the transparency of the modified starch liquefaction product is 92.3% after stored at 4° C. for 30 d, and the effect is poor.

COMPARATIVE EXAMPLE 7

A certain amount of corn starch is dissolved in water to prepare 6% (w/v) starch milk. The starch milk is gelatinized in a boiling water bath for 30 min, then cooled to room temperature, and subjected to heat preservation at 60° C. in a water bath shaker for 15 min at a speed of 160 r/min, and the pH is adjusted to 7.0. 2 U/g 1,4-α-glucan branching enzyme from *Rhodothermus obamensis* on a starch dry basis is added, treatment is carried out at 60° C. for 4 h, and enzyme deactivation is carried out by boiling. The modified corn starch is obtained by freeze drying, grinding and sieving, and re-prepared into 6% (w/v) starch milk, and the transparency is measured. The control is unmodified starch milk with the same concentration. The transparency of the modified corn starch milk is increased by 78.3% compared to the control.

What is claimed is:

1. A method for improving transparency of a starch liquefaction product, comprising:
   a) adding a 1,4-α-glucan branching enzyme to the starch liquefaction product, wherein the starch liquefaction product has a dextrose equivalent (DE) value of 11 to 15;
   b) incubating the starch liquefaction product with the 1,4-α-glucan branching enzyme at 50° C. to 70° C. for 4 hours to 24 hours;
   c) deactivating the 1,4-α-glucan branching enzyme by boiling; and
   d) dissolving the starch liquefaction product in water according to a certain concentration for preparing an aqueous solution of the starch liquefaction product;
   wherein the 1,4-α-glucan branching enzyme is derived from *Rhodothermus obamensis*, and
   wherein the starch liquefaction product is a mixture of short chain small molecule dextrin, oligosaccharides, and monosaccharide molecules obtained by hydrolyzing starch with an amylolytic enzyme, and has a concentration of 1% to 40% (w/v).

2. The method according to claim 1, wherein the DE value of the starch liquefaction product is 11.

3. The method according to claim 1, wherein the starch is selected from a group consisting of ordinary corn starch, potato starch, tapioca starch, sweet potato starch, rice starch and wheat starch.

4. The method according to claim 1, wherein a pH value of the aqueous solution of the starch liquefaction product is 5.5 to 7.5.

5. The method according to claim 1, wherein the 1,4-α-glucan branching enzyme is added in an amount of 30 to 500 U/g to the starch liquefaction product on a dry basis.

6. The method according to claim 1, wherein a sequence of a gene encoding the 1,4-α-glucan branching enzyme is set forth in SEQ ID NO: 1.

7. The method according to claim 1, wherein the starch liquefaction product is dissolved in water to prepare a 5% (w/v) aqueous solution of the starch liquefaction product, a pH value is adjusted to 6.5, the 1,4-α-glucan branching enzyme is added in an amount of 30 U/g on a dry basis, and the treatment is carried out at 60° C. for 8 hours.

8. The method according to claim 1, wherein the starch liquefaction product is dissolved in water to prepare a 5% (w/v) aqueous solution of the starch liquefaction product, a pH value is adjusted to 7.5, the 1,4-α-glucan branching enzyme is added in an amount of 100 U/g on a dry basis, and the treatment is carried out at 50° C. for 12 hours.

9. The method according to claim 1, wherein the starch liquefaction product has a DE value of 11 and is dissolved in water to prepare a 20% (w/v) aqueous solution of the starch liquefaction product, wherein pH is adjusted to 7.0, wherein the 1,4-α-glucan branching enzyme is added in an amount of 200 U/g on a dry basis, and wherein the incubating is performed at 55° C. for 24 hours.

10. The method according to claim 1, wherein the starch liquefaction product has a dextrose equivalent (DE) value of 15 is dissolved in water to prepare a 35% (w/v) aqueous solution of the starch liquefaction product, a pH value is adjusted to 7.0, the 1,4-α-glucan branching enzyme is added in an amount of 500 U/g on a dry basis, and the treatment is carried out at 65° C. for 24 hours.

\* \* \* \* \*

SEQUENCE LISTING

<160> NUMBER OF SEQ ID NOS: 1

<210> SEQ ID NO 1
<211> LENGTH: 621
<212> TYPE: PRT
<213> ORGANISM: Rhodothermus obamensis

<400> SEQUENCE: 1

```
Met Ser Trp Leu Thr Glu Glu Asp Ile Arg Arg Trp Glu Ser Gly Thr
1               5                   10                  15

Phe Tyr Asp Ser Tyr Arg Lys Leu Gly Ala His Pro Asp Asp Glu Gly
            20                  25                  30

Thr Trp Phe Cys Val Trp Ala Pro His Ala Asp Gly Val Ser Val Leu
        35                  40                  45

Gly Ala Phe Asn Asp Trp Asn Pro Glu Ala Asn Pro Leu Glu Arg Tyr
    50                  55                  60

Gly Gly Gly Leu Trp Ala Gly Tyr Val Pro Gly Ala Arg Pro Gly His
65                  70                  75                  80

Thr Tyr Lys Tyr Arg Ile Arg His Gly Phe Tyr Gln Ala Asp Lys Thr
                85                  90                  95

Asp Pro Tyr Ala Phe Ala Met Glu Pro Pro Thr Gly Ser Pro Ile Glu
            100                 105                 110

Gly Leu Ala Ser Ile Ile Thr Arg Leu Asp Tyr Thr Trp His Asp Asp
        115                 120                 125

Glu Trp Met Arg Arg Arg Lys Gly Pro Ala Ser Leu Tyr Glu Pro Val
    130                 135                 140

Ser Ile Tyr Glu Val His Leu Gly Ser Trp Arg His Lys Arg Pro Gly
145                 150                 155                 160

Glu Ser Phe Ser Tyr Arg Glu Ile Ala Glu Pro Leu Ala Asp Tyr Val
                165                 170                 175

Gln Glu Met Gly Phe Thr His Val Glu Leu Leu Pro Val Met Glu His
            180                 185                 190

Pro Tyr Tyr Gly Ser Trp Gly Tyr Gln Val Val Gly Tyr Tyr Ala Pro
        195                 200                 205

Thr Phe Arg Tyr Gly Ser Pro Gln Asp Leu Met Tyr Leu Ile Asp Tyr
    210                 215                 220

Leu His Gln Arg Gly Ile Gly Val Ile Leu Asp Trp Val Pro Ser His
225                 230                 235                 240

Phe Ala Ala Asp Pro Gln Gly Leu Val Phe Phe Asp Gly Thr Thr Leu
                245                 250                 255

Phe Glu Tyr Asp Asp Pro Lys Met Arg Tyr His Pro Asp Trp Gly Thr
            260                 265                 270

Tyr Val Phe Asp Tyr Asn Lys Pro Gly Val Arg Asn Phe Leu Ile Ser
        275                 280                 285

Asn Ala Leu Phe Trp Leu Glu Lys Tyr His Val Asp Gly Leu Arg Val
    290                 295                 300

Asp Ala Val Ala Ser Met Leu Tyr Arg Asp Tyr Ser Arg Lys Glu Trp
305                 310                 315                 320

Thr Pro Asn Ile Phe Gly Gly Arg Glu Asn Leu Glu Ala Ile Asp Phe
                325                 330                 335

Ile Lys Lys Phe Asn Glu Thr Val Tyr Leu His Phe Pro Glu Ala Met
            340                 345                 350

Thr Ile Ala Glu Glu Ser Thr Ala Trp Pro Gly Val Ser Ala Pro Thr
        355                 360                 365
```

-continued

```
Tyr Asn Asn Gly Leu Gly Phe Leu Tyr Lys Trp Asn Met Gly Trp Met
    370                 375                 380

His Asp Thr Leu Asp Tyr Ile Gln Arg Asp Pro Ile Tyr Arg Lys Tyr
385                 390                 395                 400

His His Asp Glu Leu Thr Phe Ser Leu Trp Tyr Ala Phe Ser Glu His
                405                 410                 415

Tyr Val Leu Pro Leu Ser His Asp Glu Val Val His Gly Lys Gly Ser
                420                 425                 430

Leu Trp Gly Lys Met Pro Gly Asp Asp Trp Gln Lys Ala Ala Asn Leu
            435                 440                 445

Arg Leu Leu Phe Gly His Met Trp Gly His Pro Gly Lys Lys Leu Leu
450                 455                 460

Phe Met Gly Gly Glu Phe Gly Gln His His Glu Trp Asn His Asp Thr
465                 470                 475                 480

Gln Leu Glu Trp His Leu Leu Asp Gln Pro Tyr His Arg Gly Ile Gln
                485                 490                 495

Leu Trp Val Cys Asp Leu Asn His Leu Tyr Arg Thr Asn Pro Ala Leu
                500                 505                 510

Trp His Asp Gly Pro Glu Gly Phe Glu Trp Ile Asp Phe Ser Asp Arg
        515                 520                 525

Asp Gln Ser Val Ile Cys Tyr Leu Arg Lys Asn Ala Gly Arg Met Leu
530                 535                 540

Leu Phe Val Leu Asn Phe Thr Pro Val Pro Arg Glu His Tyr Arg Val
545                 550                 555                 560

Gly Val Pro Ile Gly Gly Pro Trp His Glu Val Leu Asn Ser Asp Ala
                565                 570                 575

Val Ala Tyr Gly Gly Ser Gly Met Gly Asn Phe Gly Arg Val Glu Ala
                580                 585                 590

Val Pro Glu Ser Trp His Gly Arg Pro Phe His Leu Glu Leu Thr Leu
            595                 600                 605

Pro Pro Leu Ala Ala Leu Ile Leu Glu Pro Glu His Gly
610                 615                 620
```